US006891024B2

(12) United States Patent
Marsh

(10) Patent No.: US 6,891,024 B2
(45) Date of Patent: May 10, 2005

(54) **MONOCLONAL ANTIBODIES TO *SARCOCYSTIS NEURONA* AND USES THEREFOR**

(75) Inventor: Antoinette Marsh, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 69 days.

(21) Appl. No.: 10/140,754

(22) Filed: May 7, 2002

(65) Prior Publication Data

US 2002/0187517 A1 Dec. 12, 2002

Related U.S. Application Data

(60) Provisional application No. 60/293,603, filed on May 24, 2001, and provisional application No. 60/297,810, filed on Jun. 12, 2001.

(51) Int. Cl.[7] .................... C12P 21/08; C12P 21/04; A61K 39/002; G01N 33/53; C07H 21/04

(52) U.S. Cl. ................ 530/388.6; 424/130.1; 424/141.1; 424/151.1; 424/185.1; 424/265.1; 424/269.1; 536/23.4; 435/975; 435/810; 435/342; 435/69.7

(58) Field of Search .................... 424/141.1, 130.1, 424/151.1, 185.1, 265.1, 191.1, 269.1; 536/23.4; 435/810, 69.7, 342, 975, 7.22, 7.92, 388.6; 530/388.6

(56) References Cited

U.S. PATENT DOCUMENTS 6,344,337 B1 * 2/2002 Mansfield et al. ........... 435/7.2

OTHER PUBLICATIONS

Boothroyd et al., "The surface of Toxoplasma: more and less," *Int J. Parasitol*, 28:3–9, 1998.
Bülow and Boothroyd, "Protection of mice from fatal *Toxoplasma gundii* infection by immunization with p30 antigen in liposomes," *J. Immunol*, 147:3496–3500, 1991.
Cheadle et al., "The striped skunk (*Mephitis mephitis*) is an intermediate host for *Sarcocystis neurona*," *Int. J. Parasitol*, 31:843–849, 2001.
Ellison et al., "Molecular characterisation of a major 29 kDa surface antigen of *Sarcocystis neurona*," *International Journal for Parasitology*, 32:217–225, 2002.

Howe and Sibley, "Comparison of the major antigens of *Neospora caninum* and *Toxoplasma gondii*," *Int. J. Parasitol*, 29:1489–1496, 1999.
Marsh et al., "Comparison of the internal transcribed spacer, ITS–1, from *Sarcocystis falcatula* isolates and *Sarcocystis neurona*," *J. Parasitol*, 85(4):750–757, 1999.
Marsh et al., "Neosporosis as a cause of equine protozoal myeloencephalitis," *J. Am. Vet. Med. Assoc.*, 209(11): 1907–1913, 1996.
Marsh et al., "Description of a new species (Protozoa: *Apicomplexa: Sarcocystidae*)," *J. Parasitol*, 84(5):983–991, 1998.
Marsh et al., "Experimental infection of nude mice as a model for *Sarcocystis neurona*–associated encephalitis," *Parasitol Res.*, 83:706–711, 1997.
Marsh et al., "In vitro cultivation and experimental inoculations of *Sarcocystis falcatula* and *Sarcocystis neurona* merozoites into budgerigars (*Melopsittacus undulatus*)," *J. Parasitol*, 83(6):1189–1192, 1997.
Marsh et al., "Molecular and antigenic analysis of multiple *sarcocystis neurona* isolates obtained from horses with equine protozoal myeloencephalitis from different geographic regions," *J. Veterinary Internal Med.*, 14:12:330, Abstract #12, 2000.
Marsh et al., "Molecular and antigenic analysis of multiple *sarcocystis neurona* isolates obtained from horses with equine protozoal myeloencephalitis from different geographic regions," AAVP Proceedings from the 45th Annual Meeting, Salt Lake City, Jul. 22–25, 61, Abstract #68, 2000.
Marsh et al., "Sequence analysis and polymerase chain reaction amplification of small subunit ribosomal DNA from *Sarcocystis neurona*," *Am. J. Vet. Res.*, 57(7):975–981, 1996.
Parmley et al., "Two alleles of the gene encoding surface antigen p22 in 25 strains of *Toxoplasma gondii*," *J. Parasitol*, 80(2):293–301, 1994.
Ware and Kasper, "Strain–specific antigens of *Toxoplasma gondii*," *Infect. Immun.*, 55:778–783, 1987.

* cited by examiner

*Primary Examiner*—L. F. Smith
*Assistant Examiner*—Padma Baskar
(74) *Attorney, Agent, or Firm*—Fulbright & Jaworski, LLP

(57) ABSTRACT

The present invention is directed to particular monoclonal antibodies that find use in the identification and purification of *Sarcocystis neurona* and related antigens. In particular, these antibodies permit the diagnosis of *Sarcocystis* related diseases such as equine protozoal myeloencephalitis (EPM).

11 Claims, No Drawings

MONOCLONAL ANTIBODIES TO *SARCOCYSTIS NEURONA* AND USES THEREFOR

The present application claims priority to U.S. Provisional Application Ser. No. 60/293,603, filed May 24, 2001, and U.S. Provisional Application Ser. No. 60/297,810, filed Jun. 12, 2001, both of which are incorporated by reference in their entirety.

The government owns rights in the present invention pursuant to grant number DHHS 1 R15 AI4478-01 from the National Institutes of Health.

BACKGROUND OF THE INVENTION

1. Field of the Invention

The present invention relates generally to the fields of microbiology, immunology and pathology. More particularly, it concerns the development of particular monoclonal antibodies for use in the diagnosis and therapy of disease caused by *Sarcocystis neurona* infections.

2. Description of Related Art

Equine protozoal myeloencephalitis (EPM) is a widespread neurological disease in horses. Similar syndromes have been recognized in other species, such as marine mammals. It is progressive and in advanced stages, the horse will suffer from spinal cord and brain stem damage resulting in ataxia of the limbs and other signs of muscular incoordination, loss of response to certain sensory stimuli and muscle atrophy. In severe cases of recurrent neurological signs that do not respond to therapy, horses must be euthanized, which is very costly to owners.

Most cases of EPM are caused by a protozoan parasite, *Sarcocystis neurona*. This organism has been identified in other species and has been associated with encephalitis as well. The horse is thought to become infected with this parasite by ingestion of sporocysts shed by the opossum (*Didelphis virginiana*) or closely related species that are found in the Americas. This would suggest that horses shipped to other parts of the world could develop EPM later; therefore, EPM is not just a disease found in the Americas.

To date, there has been only one group—the inventors—that have disclosed a monoclonal antibody directed *Sarcocystis neurona*. Marsh et al. (2000). However, this report did not disclose the target for the antibody or how it was made. In addition, the antibody failed to react with certain strains of *S. neurona*, suggesting limited suitability for use in diagnostic screens. Thus, there clearly remains a need to identify additional antibodies that can be used in both diagnosis and therapy of *S. neurona* disease.

SUMMARY OF THE INVENTION

Thus, in accordance with the present invention, there is provided a monoclonal antibody that binds immunologically to a *Sarcocystis neurona* organism or antigen, designated 2A7-18 or 2G5-2. The antibody may comprise a label, for example, a radioisotope, bead, a ligand, a chemilluminescent molecule, a fluorescent molecule, or an enzyme. It may also comprise a therapeutic compound, such as a radioisotope or a chemotherapeutic.

In another embodiment, there is provided a method of identifying a *Sarcocystis neurona* organism or antigen in a sample comprising (a) contacting the sample with a monoclonal antibody that binds immunologically to a *Sarcocystis neurona* organism or antigen, designated 2G5-2 or 2A7-18; and (b) determining binding of the monoclonal antibody to a *Sarcocystis neurona* organism or antigen in the sample, whereby binding of the monoclonal antibody indicates the presence of *Sarcocystis neurona* organism or antigen. The sample may be obtained from a warm-blooded animal, such as a horse, cow, dog, cat, mink, raccoon, skunk, harbor seal, sea otter, mouse, armadillo or human. The sample may be a tissue sample, a fluid sample or a fecal sample. The tissue sample may be from brain, spinal cord, placenta, lung, liver, muscle, connective tissue, vascular endothelium or gastrointestinal tract. The fluid sample may be from blood, serum, plasma, urine, milk, ascites, cerebrospinal fluid or fetal fluid.

The assay format may be a Western blot, a radioimmunoprecipitation, RIA, or an ELISA, including a sandwich ELISA. The method may employ a solid support such as a column, a dipstick, a filter or a microtiter dish. The ELISA may comprise detection of bound 2G5-2 or 2A7-18 using a labeled anti-Ig antibody. The ELISA also may be is a competitive assay. The assay also may involve quantification. The assay may further comprise determining antigenic profile of the *Sarcocystis neurona* organism.

In yet another embodiment, there is provided a kit comprising at least one a monoclonal antibody that binds immunologically to a *Sarcocystis neurona* organism or antigen, designated 2A7-18 or 2G5-2, in suitable container. The kit may comprise both 2A7-18 and 2G5-2. The antibody may comprise a label, for example, a bead, a radioisotope, a ligand, a chemilluminescent molecule, a fluorescent molecule, or an enzyme.

In still yet another embodiment, there is provided a method of detecting the presence, in a sample, of antibodies that bind immunologically to a *Sarcocystis neurona* organism or antigen, comprising (a) providing a test composition comprising a *Sarcocystis neurona* organism or antigen; (b) contacting the test composition with a known amount of a monoclonal antibody that binds immunologically to a *Sarcocystis neurona* organism or antigen, designated 2G5-2 or 2A7-18, the monoclonal antibody comprising a detectable label; (c) contacting the product of step (b) with the sample; and (d) measuring a change in the amount of label associated with the test composition, as compared to the amount observed in step (b), wherein a decrease in the amount of label associated with the test composition indicates the presence of antibodies that bind immunologically to a *Sarcocystis neurona* organism or antigen in the sample. The measuring of change may be quantitative. The label may be an enzyme label, a radiolabel, a chemilluminescent label or a fluorescent label.

In yet a further embodiment, there is provided a method of isolating a *Sarcocystis neurona* organism or antigen comprising (a) providing a monoclonal antibody that binds immunologically to a *Sarcocystis neurona* organism or antigen, designated 2G5-2 or 2A7-18; (b) contacting the antibody with a sample containing a *Sarcocystis neurona* organism or antigen; and (c) isolating the antibody from the sample, whereby isolation of the antibody also isolates the *Sarcocystis neurona* organism or antigen. The antibody may be bound to a support, for example, a column, a dipstick, a filter or a plate. The antibody also may comprise a label that permits isolation thereof.

The method may further comprise isolating the *Sarcocystis neurona* organism or antigen away from the monoclonal antibody. The monoclonal antibody may further comprise a label that permit isolation of the antibody, such as a bead, a chemilluminescent or fluorescent tag or a ligand. The isolating step may comprise affinity chromatography, fluorescence activated cell sorting, precipitation or centrifugation.

In still yet a further embodiment, there is provided a method of treating a horse for equine protozoal myeloencephalitis (EPM) comprising (a) obtaining a tissue or fluid sample from the horse; (b) contacting the sample with a monoclonal antibody that binds immunologically to a *Sarcocystis neurona* organism or antigen, the antibody designated 2G5-2 or 2A7-18; (c) determining binding of the monoclonal antibody to a *Sarcocystis neurona* organism or antigen in the sample; and (d) in the event that a *Sarcocystis neurona* organism or antigen is identified in the sample, treating the horse for EPM.

DESCRIPTION OF ILLUSTRATIVE EMBODIMENTS

I. The Present Invention

The present invention is directed to the identification of two particular antibodies against *Sarcocystis neurona* and antigens thereof. This application provides the first enabling disclosure for antibodies to *Sarcocystis neurona*. In addition is provides for the use of these antibodies, both individually and in combination, in the screening of samples for a *Sarcocystis neurona* organism, antigen or antibodies. This is particularly important as *Sarcocystis neurona* is a significant pathogen for horses, where it is the cause of equine protozoal myeloencephalitis, or "EPM." The details of the invention are provided below.

II. *Sarcocystis Neurona* and Equine Protozoal Myeloencephalitis (EPM)

*Sarcocystis neurona* is a coccidian protozoan that exhibits a wide geographic distribution, including North and South America, as well as parts of the Old World. It has a number of hosts including opossum (definitive host), skunks, armadillos, cats (intermediate host) and horses (accidental host). Sites of infection include the intestinal lining (carnivore host), skeletal muscle (intermediate hosts) and brain & spinal cord (horses).

Horses are infected by ingesting infective *S. neurona* sporocysts. *Sarcocystis neurona* has an obligate 2-host species life cycle, including the natural intermediate host which is a prey species of some kind, and a definitive host, the opossum. Until recently, *S. neurona* was considered likely to be *S. falcatula*, a species of Sarcocystis that utilizes birds of passerine (grackles, cowbirds, starlings), psittacine (budgerigars) or columborid (pigeons) birds as intermediate hosts, but recent research conducted at the University of Florida, the University of California, the University of Missouri and Cornell University has revealed that *S. neurona* and *S. falcatula* are not the same species. However, the opossum (*Didelphis virginiana*) is the definitive host for both species, and is the source of the infective sporocysts to horses. The parasite encysts in the muscle tissue of the intermediate host. When this tissue is eaten by opossums, the organism undergoes sexual reproduction in intestinal epithelium, and forms infective sporocysts contained within an oocyst. Oocysts and sporocysts are found in the intestinal contents but the fragile oocyst is commonly disrupted by the time feces are passed. The intermediate host becomes infected by ingesting sporocysts which presumably contaminate the feed or water. Sporozoites emerge from the sporocysts, penetrate the intestines, and become tachyzoites (merozoites), which undergo a series of replicative cycles in the vascular endothelial cells, and possibly white blood cells. The protozoa enter host cells, and become the intracellular stage, the schizont, or meront. This schizont is a "mother cell" that divides asexually into many tachyzoite offspring.

In the natural intermediate hosts, later generations of tachyzoites migrate to muscle, and encyst in myocytes, forming sarcocysts. These later generations of tachyzoites develop into a slowly dividing stage, called bradyzoites. Bradyzoites divide slowly over the course of the host's lifetime. Some species of Sarcocystis cause myositis in the intermediate host (e.g., eosinophilic myositis caused by *S. cruzi* in cattle) while others evade the host immune system, and remain asymptomatic (e.g., *S. fayeri* in horses is rarely associated with myositis). When the natural intermediate host is killed, or dies and is eaten, these cysts are activated in the gastrointestinal tract of the definitive host, and the cycle starts again. Most *Sarcocystis* spp. are found encysted in the muscle tissue of the intermediate host, but some *Sarcocystis* spp., as well as the closely related protozoa, *Toxoplasma gondii*, have been found in cysts in the central nervous system.

Horses are an aberrant intermediate host of *S. neurona*. Sporocysts are eaten, pass into the small intestines and excyst in the horse. From there, the infective stage of the organism, the sporozoites, enter the horse's blood stream. In some horses, they undergo several replicative cycles in endothelial cells (in blood vessels), becoming tachyzoites, and migrate to the central nervous system. They replicate asexually within neurons and microglial cells, without forming tissue cysts. In the central nervous system of the horse, they slowly divide and grow, gradually destroying the nervous tissue, causing incoordination and the other clinical signs that result from EPM. The stage of the organism found horses cannot be transmitted to other horses. Because the organism does not encyst in the tissues, it cannot be transmitted to opossums, even if the opossum were to eat the tissue. Therefore, the horse is a dead end host for the protozoan.

Diagnosis is limited, relying on unexplained neurologic symptoms, and testing spinal fluid for antibodies. Treatment recommendations vary; however, the trends if toward: (a) trimethoprim-sulfadiazine, 15–25 mg/kg of body weight, orally, every 12 hours for at least 12 weeks; (b) pyrimethamine (Daraprim), 1.0 mg/kg orally, every 24 hours for at least 12 weeks; (c) rest and minimizing of stress; and (d) anti-inflammatories. While most horses respond to treatment, few make a complete recovery.

III. Producing Monoclonal Antibodies

It will be understood that monoclonal antibodies binding to *S. neurona* and related proteins will have utilities in several applications. These include the production of diagnostic kits for use in detecting and diagnosing disease. In these contexts, one may to link such antibodies to diagnostic or therapeutic agents, or use them as capture agents or competitors in competitive assays. Means for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC,-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations; and U.S. Pat. No. 4,867,973 which describes antibody-therapeutic agent conjugates.

IV. Antibody Conjugates

Antibodies of the present invention may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemilluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium186, rhenium$^{188,}$ $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al, 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fe region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fe region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present invention concerns immunodetection methods for binding, purifying, removing, quantifying and otherwise generally detecting *Sarcocystis neurona* and its associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of *S. neurona* antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing *S. neurona*, and contacting the sample with a first antibody in accordance with the present invention, as the case may be, under conditions effective to allow the formation of immunocomplexes.

These methods include methods for purifying *S. neurona* or related antigens from a sample. The antibody will preferably be linked to a solid support, such as in the form of a column matrix, and the sample suspected of containing the *S. neurona* or antigenic component will be applied to the immobilized antibody. The unwanted components will be washed from the column, leaving the *S. neurona* antigen immunocomplexed to the immobilized antibody, which is then collected by removing the organism or antigen from the column.

The immunobinding methods also include methods for detecting and quantifying the amount of *S. neurona* or related components in a sample and the detection and quantification of any immune complexes formed during the binding process. Here, one would obtain a sample suspected of containing *S. neurona* or its antigens, and contact the sample with an antibody that binds *S. neurona* or components thereof, followed by detecting and quantifying the amount of immune complexes formed under the specific conditions. In terms of antigen detection, the biological sample analyzed may be any sample that is suspected of containing *S. neurona* or S. neurona antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *S. neurona* or antigens present. After this time, the sample-antibody antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the *S. neurona* or *S. neurona* antigen is added to the wells. After binding and washing to remove non-specifically bound immune complexes, the bound antigen may be detected. Detection may be achieved by the addition of another anti-*S. neurona* antibody that is linked to a detectable label. This type of ELISA is a simple "sandwich ELISA." Detection may also be achieved by the addition of a second anti-*S. neurona* antibody, followed by the addition of a third antibody that has binding affinity for the second antibody, with the third antibody being linked to a detectable label.

In another exemplary ELISA, the samples suspected of containing the *S. neurona* or *S. neurona* antigen are immobilized onto the well surface and then contacted with the anti-*S. neurona* antibodies of the invention. After binding and washing to remove non-specifically bound immune complexes, the bound anti-*S. neurona* antibodies are detected. Where the initial anti-*S. neurona* antibodies are linked to a detectable label, the immune complexes may be detected directly. Again, the immune complexes may be detected using a second antibody that has binding affinity for the first anti-*S. neurona* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present invention contemplates the use of competitive formats. This is particularly useful in the detection of S. neurona antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled S. neurona monoclonal antibodies to determine the amount of S. neurona antibodies in a sample. The basic format would include contacting a known amount of S. neurona monoclonal antibody (linked to a detectable label) with S. neurona antigen or organism. The *S. neurona* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

2. Immunohistochemistry

The antibodies of the present invention may also be used in conjunction with both fresh-frozen and/or formalin-fixed, paraffin-embedded tissue blocks prepared. for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

3. Immunodetection Kits

In still further embodiments, the present invention concerns immunodetection kits for use with the immunodetection methods described above. As the *S. neurona* antibodies are generally used to detect *S. neurona* or *S. neurona* antigens, the antibodies will be included in the kit. The immunodetection kits will thus comprise, in suitable container means, a first antibody that binds to *S. neurona* or *S. neurona* antigen, and optionally an immunodetection reagent.

In certain embodiments, the *S. neurona* antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention.

The kits may further comprise a suitably aliquoted composition of the *S. neurona* or *S. neurona* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present invention will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Examples 1

Example

*Sarcocystis neurona* merozoites were continuously cultured in bovine turbinate with RPMI media (Gibco/BRL, Gaithersburg, Md.) as previously described (Marsh et al., 1996). Cell culture supernatant containing large numbers of free merozoites were harvested from culture, washed, enumerated, and resuspended in phosphate buffered saline (PBS). Six-week old Balb/c mice were inoculated intraperitoneally with $2\times10^5$ merozoites per inoculation (Mouse 1: live parasites on days 1, 32 and 54; or Mouse 2: sonicated mixture of parasites with Freund's adjuvant (initial injection), incomplete adjuvant (second injection) and live parasites (third injection) on days 1, 32 and 80). Pre-immune serum was obtained and compared with hyperimmune serum to ensure specificity of screening. Splenocytes were obtained on Day 57 (Mouse 1) or day 83 (Mouse 2) for fusion with a murine myeloma cell line as described. Rogers et al. (1997).

For screening clones, monoclonal culture media was removed from cell wells. The media containing antibodies was screened by double-system enzyme-linked immunosorbent assay (ELISA). The top portion (4 rows) of an ELISA plate is coated with S. neurona merozoites antigen and the bottom portion (4 rows) is coated with host cell antigen in carbonated ELISA coating buffer using immunology ELISA protocol. High titer and pre-inoculation sera from the mice served as positive and negative controls. Aliquots were washed and peroxidase-affinity purified goat anti-mouse IgG (subclasses 1+2a+2b+3) Fc fragment antibody (Jackson Laboratories, West Grove, Pa.), followed by development with ABTS peroxidase substrate (Kirkegaard & Perry Laboratories, Gaithersburg, Md.) was used to detect reactive wells. IgG (Fc fragment) specific antibody was used for specific selection of IgG antibody isotype rather than other possible isotypes such as IgM and IgA. The double ELISA method was used to discard clones that react with host cell material. Individual clones were selected, expanded, and repeat double ELISA method testing done.

Specific clones 2A7 and 2G5 were further subcloned into single cell populations into each well of a 96-well plate. Briefly, cloning was performed by flow cytometry using a FACSVantage flow cytometer (Becton Dickinson, San Jose, Calif.) as opposed to limiting dilution. The instrument was aligned using DNA-Check fluorospheres (Coulter Immunology, Miami, Fla.) with coefficients of variation (CVs) kept at 2% or less at 200 mW output from a 4-watt argon laser tuned to 488 nm. Sorting was performed by depositing one cell per well into 200 $\mu$l of cell culture media in a 96 well tissue culture plate using the Automatic Cell Deposition Unit and Clone-Cyt software (Becton Dickinson). Only viable single cells were sorted by gating on a dual parameter histogram of forward scatter versus log side scatter. Subclones were then tested by an ELISA using S. neurona merozoite antigen lysate and host monolayer control lysate coated plates. These clones were expanded, repeated tested for reactivity, and reactive clones derived from single cell origin were used for large scale production of monoclonal antibody containing media. High titer monoclonal antibody (2A7-18 & 2G5-2) was generated in Celline CL1000 flasks as recommended by the manufacturer (Integra Biosciences, Ijamsville, Md.). IgG was quantified using a capture ELISA developed at the University of Missouri, Veterinary Pathobiology, using a modification of the isotype determination kit. In addition, total protein was measured using the Lowry method.

The isotype of 2A7-18 and 2G5-2 was determined to be $IgG_1$ with kappa light chain using a commercially available kit (Zymed Laboratories, South San Francisco, Calif.). Monoclonal antibodies were tested by western blot technique, immunofluorescence antibody assay, and an immunohistochemistry assay on S. neurona-infected mouse tissues.

Immunoblot and immunofluorescence analysis. Culture-derived S. neurona, Sarcocystis falcatula, N. hughesi or Toxoplasma gondii were lysed in non-reducing sample buffer. The parasite isolates have been previously described (Sabin, 1941; Marsh et al., 1996a; 1996b; 1997a; 1997b; 1998; 1999). Proteins were separated by gel electrophoresis, transferred to nitrocellulose membranes, and blocked with Tris-buffered saline containing 0.1% Tween 20 (T-TBS) and 5% (w/v) nonfat dry milk (Laemmli, 1970; Gallagher and Smith, 1995). Pre-immune and hyperimmune sera (rabbit or mouse) were used as positive controls and compared with the mAbs (Marsh et al., 1996b). Samples were loaded into individual lanes of the Western blot apparatus (Immunetics, Cambridge, Mass.) or incubated with membrane in individual containers. The membranes were probed for 1 h at 22–24° C. (apparatus) or overnight at 4° C. (individual strips). The membranes were removed and washed in T-TBS. A peroxidase-conjugated anti-rabbit IgG (Jackson ImmunoResearch, West Grove, Pa.) or anti-mouse IgG (Jackson) was used, followed by washes and development using an enhanced chemiluminescent detection system (Amersham Pharmacia, Piscataway, N.J.). To determine if the epitopes recognized were a carbohydrate moiety, membranes were treated with 5 mM sodium periodate prior to the blocking step (Woodward et al., 1985).

For immunofluorescent staining, culture-derived parasites (S. neurona, S. falcatula, N. hughesi, and T. gondii) were aliquoted onto multi-well slides or into Eppendorf tubes for fixed and live parasite immunofluorescent staining, respectively. Parasites were fixed and permeabilized on indirect fluorescence antibody (IFA) slides using 10% (v/v) phosphate buffered formalin in PBS. Fixed or live parasites were incubated with polyclonal antibody (terminal bleed of mouse), mAb 2A7-18 or mAb 2G5-2 for 1 h at 37° C. in a humid chamber. Negative controls included substituting monoclonal culture medium not containing parasite antibodies or PBS in the primary antibody step. Unbound antibodies were washed away in PBS. Live parasites were then aliquoted onto multi-well slides, air-dried, and the anti-mouse fluorescein-labeled antibody was used to detect the antibodies bound to the parasites on the slides.

Immuno-electron microscopy. Immuno-electron microscopy (EM) was performed with mAbs 2A7-18 and 2G5-2 to determine if the antibody-antigen reactivity could be localized to parasite intracellular components or surface membrane of extracellular S. neurona merozoites. Culture-derived extracellular and intracellular S. neurona (UCD-SN1) merozoites were harvested from cell culture flasks, washed twice with calcium and magnesium-fee PBS and fixed with 4% paraformaldehyde, 0.1% glutaraldehyde in 0.1 M cacodylate buffer (0.08 M sucrose, 0.02 M CaCl2) for 1 h at RT. Pellets were washed in cacodylate buffer, dehydrated in ethanol and embedded in LR white and Uni-cryl resin. Ultrathin sections were transferred to nickel grids and blocked with 2 mM Tris, 2 mM NaN3, 0.9% NaCl, 0.1% fetal bovine serum albumin for 1 h. The sections were incubated overnight with mAb 2A7-18 or mAb 2G5-2 at two concentrations: undiluted and a 200-fold dilution in blocking buffer at 4° C. The sections were then washed ten times in the blocking buffer followed by incubation with secondary antibody (10 nm gold conjugated anti-mouse IgG, Sigma, St. Louis, Mo.) at 37° C. for 4 h. After counter staining with 1% lead citrate and 1% uranyl acetate, the sections were examined using a JEOL 1200EX electron microscope.

Immunohistochemistry. All immunohistochemistry was performed using the Dako Envision+Peroxidase system as described (Suedmeyer et al. 2002) with the exception that the Dako Envision+Peroxidase Rabbit kit was replaced with the Dako Envision+Peroxidase Mouse kit for the mAbs. MAbs 2A7-18 and 2G5-2 were initially screened (1:100) for their immunohistochemical reactivity and optimal dilutions to both S. neurona and S. falcatula merozoites using paraffin-embedded horse spinal cord naturally infected with S. neurona (Marsh et al. 1996b) and budgerigar lung experimentally infected with S. falcatula (Marsh et al. 1997b). Monoclonal antibody 2G5-2 was tested at additional dilutions of 1:200, 1:800 and 1:1,600. Paired control tissues were simultaneously tested against polyclonal antisera to S. neurona (1:1,600) and S. falcatula (1:1,600) for comparison.

Following determination of the optimal dilution for mAbs 2A7-18 and 2G5-2, both mAbs and the corresponding Sarcocystis polyclonal antibodies were tested and their reactivities compared using the control tissues listed above, plus paraffin-embedded tissues as follows: mouse brain experimentally infected with a California isolate of *S. neurona* (Marsh et al. 1996b), ovine placenta naturally infected with *T gondii* tachyzoites, canine muscle naturally infected with *Neospora caninum* tachyzoites (Marsh et al. 1996a), and bovine tongue naturally infected with *Sarcocystis cruzi* bradyzoites (kindly provided by Dr. J. P. Dubey).

Example 2

Results and Discussion

Immunoblot and immunofluorescence analysis. The polyclonal antibodies and the two monoclonal antibodies all appeared to recognize similar molecular-sized immunodominant proteins in both naturally and experimentally *S. neurona*-infected animals (Cheadle et al., 2001; Marsh et al., 2001). Each mAb reacted to a different band of separated *S. neurona* antigens. MAbs 2A7-18 and 2G5-2 recognized proteins of approximately 28 kDa and 14 kDa, respectively. The epitopes were not carbohydrate moieties as reactivity was not lost after periodate treatment. The polyclonal anti-*S. neurona* antibody reacted with reduced *S. neurona* antigen whereas mAb 2A7-18 and mAb 2G5-2 did not. MAb 2A7-18 reacted with *S. neurona* isolates obtained from horses in California but did not react with one (SN-MU1) of the two *S. neurona* isolates obtained from horses in Missouri; however, mAb 2G5-2 recognized all the *S. neurona* isolates tested. The immunoblots indicate slight differences in the molecular size of this approximately 14 kDa protein. Exact molecular sizes are difficult to discern under the conditions used. The results show antigenic variation of the two *S. falcatula* isolates as mAb 2A7-18 reacted with the *S. falcatula* UCD-1 (California) isolate but not the *S. falcatula* Flo1 (Florida) isolate, and mAb 2G5-2 reacted with both *S. falcatula* isolates. The intensity of staining was stronger with SF-Flo 1 as compared to SF-UCD 1. The *S. falcatula* proteins recognized were of similar molecular size. When the immunoblots were reprobed with rabbit polyclonal anti-*S. neurona* antibodies, both immunodominant proteins were visible in all the Sarcocystis isolates except SN-MU1. The immunoblot with mAb 2G5-2 indicates that SN-MU1 antigens were present in concentrations comparable to those of the other Sarcocystis antigens. *Toxoplasma gondii*, *N. hughesi* or host cell antigens showed no reactivity by immunoblot analysis when probed with mAb 2A7-18 and mAb 2G5-2 at any of the dilutions evaluated.

By IFA, mAb 2A7-18 reacted to the surface of live and fixed *S. neurona* merozoites but not to the other parasites tested. MAb 2G5-2 required the *S. neurona* merozoites to be fixed for reactivity as live staining of parasites showed little reactivity with this antibody. No IFA staining was seen with mAb 2G5-2 when tested against the other parasites.

Immuno-electron microscopy. Immuno-EM studies indicated that mAb 2A7-18 labeling is less abundant and appeared to be associated primarily with the surface membrane whereas mAb 2G5-2-labeled proteins appeared to be dispersed in the parasite. In some sections, mAb 2G5-2 labeling was concentrated within intracellular vesicles of *S. neurona* merozoites. When both primary antibodies were diluted 200-fold, the reactivity of mAb 2A7-18 was dramatically reduced while that of mAb 2G5-2 was still obvious. Little unbound secondary antibody was observed in negative control (no specific primary mAb) specimens containing *S. neurona*.

Immunohistochemistry. MAb 2A7-18 reacted positively by immunohistochemistry to select schizonts or merozoites of *S. falcatula* within the budgerigar lung at a dilution of 1:100 and this reactivity began to diminish at a 1:200 dilution. It did not react with *S. neurona* merozoites at either screening dilution. A dilution of 1:100 was considered optimal and used for further study. MAb 2G5-2 reacted strongly positive to *S. neurona* schizonts and merozoites in both horse spinal cord and experimentally infected nude mouse brain at both screening dilutions but did not react to *S. falcatula* schizonts or merozoites at either dilution. The strong positive reaction continued to a dilution of 1:1,600 in experimentally infected tissue but was variable in intensity within the naturally infected horse spinal cord. All stages of parasite schizogony within the horse spinal cord reacted strongly positive at 1:800 with no detectable background staining. A 1:800 dilution was considered the optimal dilution range and was used for further study.

When the reactivity of these mAbs was tested against a larger bank of tissues containing related protozoans, mAb 2A7-18 continued to demonstrate positive reactivity only to select meronts of *S. falcatula* within infected budgerigar lung but did not react with *S. neurona* meronts, *S. cruzi* bradyzoites, *T. gondii* tachyzoites, or *N. caninum* tachyzoites. Monoclonal antibody 2G5-2 reacted strongly positive with the meronts of *S. neurona* in horse spinal cord and mouse brain but did not react with any of the other protozoa. There was no appreciable background in any of the tissues, including nude mouse tissues, using the Envision+ Peroxidase Mouse system. Polyclonal sera raised in rabbits against whole *S. neurona* reacted strongly to *S. neurona*, but also showed an inconsistent pattern of reactivity from negative to occasional weak positive reactions with *S. falcatula* meronts. *S. falcatula* polyclonal antisera reacted positively to both *S. falcatula, S. neurona* meronts, and weakly to *S. cruzi* bradyzoites. These polyclonal antisera did not react to the other protozoa.

Discussion. The immunofluorescence and immuno-EM results suggest that mAb 2A7-18 reacts with a surface protein of *S. neurona* whereas mAb 2G5-2 to react with an internal antigen of *S. neurona*. The molecular size of the antigen recognized 2A7-18 is approximately 28 kDa This protein is immunodominant, and it could be analogous to the p30 major surface antigen (SAG), TgSAG-1, of *T. gondii* or another SAG or SAG-related sequence family of proteins described for *T. gondii* and *Neospora* (Büilow and Boothroyd 1991; Parmley et al. 1994; Boothroyd et al. 1998; Howe and Sibley 1999; Marsh et al. 1999). Antigenic differences detected in the *S. neurona* isolates would also be analogous to antigenic differences that have been reported for TgSAG-1 (Ware and Kasper 1987; Büilow and Boothroyd 1991; Parmley et al. 1994). The immunoblot results were surprising as mAb 2A7-18 recognized *S. falcatula* (UCD-1) whereas it did not recognize *S. falcatula* (Flo1) indicating again that antigen variation is occurring in closely related isolates of *S. falcatula*. These two isolates were derived from distinct geographic regions: western and eastern areas of North America (Marsh et al. 1999). Moreover, the epitope recognized by mAb 2A7-18 must be exposed in *S. falcatula* by the immunoblot procedure and to a limited extent in the immunohistochemistry but not in the IFA procedure used in this study since no reactivity was seen using IFA. It was disappointing, but not surprising, that mAb 2A7-18 did not react with *S. neurona*-infected paraffin-embedded tissues as antigen epitopes can be destroyed by formalin-fixation and subsequent steps for paraffin-embedding (Ramos-Vara and Beissenherz 2000). Therefore, mAb 2A7-18 appears to have diagnostic limitations since it only reacted to a limited number of S. neurona isolates tested and did not perform well with paraffin-embedded S. neurona infected tissues. It would be important to determine if the protein recognized by mAb 2A7-18 is stage-specific, like TgSAG-1, or can be found at other life-stages, such as sporozoites and bradyzoites, of the S. neurona isolates recognized.

The mAb 2G5-2 appears to recognize a more conserved epitope amongst the S. neurona isolates than mAb 2A7-18 since it recognizes an epitope present in all the isolates evaluated, which came from distinct geographic regions, and a similar epitope in both S. falcatula isolates, indicating this epitope is exposed during the immunoblot procedure. This epitope exposure did not occur when the tissues were processed for immunohistochemistry or IFA since no reactivity was seen with mAb 2G5-2 to S. falcatula under those conditions. More importantly, the S. neurona epitope is still recognized by mAb 2G5-2 after S. neurona-infected tissues are formalin-fixed and paraffin-embedded. This would suggest that mAb 2G5-2 would be a useful antibody for immunohistochemistry staining for post-mortem specimens and for more specific identification of this species of protozoa. This antibody will be of great assistance in determining the range of susceptible hosts for S. neurona. Additional studies are needed to determine the protein sequence recognized by these mAbs.

Example 3

ATCC Deposit Information and Antibody Information

| Clone | Isotype | Date of Deposit | Accession No. |
|---|---|---|---|
| 2A7-18 | IgG$_1$ | May 31, 2001 | PTA-3418 |
| 2G5-2 | IgG$_1$ | May 31, 2001 | PTA-3419 |

American Type Culture Collection (ATCC)

P.O. Box 1549

Manassas, Va. 20108 USA

Antibody 2A7-18 recognizes the immunodominant protein of approximate molecular size of 29 kDa present in S. neurona (UCD1, UCD 2 and UCD 3). These three isolates are all from the west coast of the United States. The antibody 2A7-18 does not recognize two S. neurona isolates from Missouri.

The antibody 2G5-2 recognizes the approximately 14 kDa immunodominant protein present in all S. neurona isolates tested to date. The proteins recognized by both antibodies cannot be reduced as the antibodies will no longer recognize the proteins. However, the proteins can be denatured and still be recognized by both antibodies. Antibody 2G5-2 recognizes the S. neurona merozoite antigen after formalin-fixation followed by paraffin-embedding of tissues containing S. neurona merozoites. In addition, antibody 2G5-2 will react specifically with the tissue cyst wall of a S. neurona-like agent but not the internal bradyzoites after the parasite infected tissue has been formalin-fixed and paraffin-embedded. Therefore, antibody 2G5-2 can be used in a diagnostic immunohistochemical staining procedure on both naturally- and experimentally-infected tissues.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,816,567
U.S. Pat. No. 4,867,973
U.S. Pat. No. 4,938,948
U.S. Pat. No. 5,021,236
U.S. Pat. No. 5,196,066
U.S. Pat. No. 5,565,332

Abbondanzo, Medeiros, Cossman, "Molecular genetics and its application to the diagnosis and classification of hematopoietic neoplasms," Am. J. Pediatr. Hematol. Oncol., 12(4):480–489, 1990.

Allred, Bustamante, Daniel, Gaskill, Cruz, "Immunocytochemical analysis of estrogen receptors in human breast carcinomas. Evaluation of 130 cases and review of the literature regarding concordance with biochemical assay and clinical relevance," Arch. Surg., 125(1):107–113, 1990.

"Antibodies: A Laboratory Manual," Cold Spring Harbor Press, Cold Spring Harbor, N.Y., 1988.

Atherton et al., Biol. of Reproduction, 32, 155–171, 1985.

Boothroyd et al., "The surface of Toxoplasma: more and less," Int J. Parasitol, 28:3–9, 1998.

Brown et al., J. Immunol. Meth., 12;130(1):111–121, 1990.

Bülow et al., "Protection of mice from fatal Toxoplasma gundii infection by immunization with p30 antigen in liposomes," J. Immunol, 147:3496–3500, 1991.

Campbell, In: Monoclonal Antibody Technology, Laboratory Techniques in Biochemistry and Molecular Biology, Vol. 13, Burden and Von Knippenberg, Eds. pp. 75–83, Amsterdam, Elseview, 1984.

Cheadle et al., "The striped skunk (Mephitis mephitis) is an intermediate host for Sarcocystis neurona," Int. J Parasitol, 31:843–849, 2001.

De Jager et al., "Current status of cancer immunodetection with radiolabeled human monoclonal antibodies" Semin. Nucl. Med. 23(2):165–179, 1993.

Dholakia et al., J. Biol. Chem., 264, 20638–20642, 1989.

Doolittle and Ben-Zeev, "Immunodetection of lipoprotein lipase: antibody production, immunoprecipitation, and western blotting techniques" Methods Mol. Biol., 109:215–237, 1999.

Gallagher et al., "Electrophoretic separation of proteins," In: Coligan et al. (eds) *Current Protocols in Immunology*, vol2. Wiley, New York, pp 8.4.1–8.4.21, 1995.

Gefter, Margulies, Scharff, "A simple method for polyethylene glycol-promoted hybridization of mouse myeloma cells," *Somatic Cell Genet.*, 3:231–236, 1977.

Goding, In: *Monoclonal Antibodies: Principles and Practice*, 2d ed., Orlando, Fla., Academic Press, 60–61, 65–66, 71–74, 1986.

Gulbis and Galand, "Immunodetection of the p21-ras products in human normal and preneoplastic tissues and solid tumors: a review" *Hum. Pathol.* 24(12):1271–1285, 1993.

Howe et al., "Comparison of the major antigens of *Neospora caninum* and *Toxoplasma gondii*," *Int. J Parasitol* 29:1489–1496, 1999

Khatoon et al., *Ann. of Neurology*, 26, 210–219, 1989.

King et al., *J. Biol. Chem.*, 269, 10210–10218, 1989.

Kohler and Milstein, "Continuous cultures of fused cells secreting antibody of predefined specificity," *Nature*, 256:495–497, 1975.

Kohler and Milstein, "Derivation of specific antibody-producing tissue culture and tumor lines by cell fusion," *Eur. J Immunol*, 6:511–519, 1976.

Laemmli, "Cleavage of structural proteins during the assembly of the head of bacteriophage T4," *Nature* 227:680–685, 1970.

Marsh et al., "Neosporosis as a cause of equine protozoal myeloencephalitis," *J. Am. Vet. Med. Assoc.*, 209: 1907–1913, 1996a.

Marsh et al., "Sequence analysis and polymerase chain reaction amplification of small subunit ribosomal DNA from *Sarcocystis neurona*," *Am. J. Vet. Res.* 57–975–981, 1996b.

Marsh et al., "Experimental infection of nude mice as a model for *Sarcocystis neurona*-associated encephalitis," *Parasitol Res.* 83–706–711, 1997a.

Marsh et al., "In vitro cultivation and experimental inoculations of *Sarcocystis falcatula* and *Sarcocystis neurona* merozoites into budgerigars (*Melopsittacus undulatus*)," *J. Parasitol* 83:1189–1192, 1997b.

Marsh et al., "Description of a new species (Protozoa: Apicomplexa: Sarcocystidae)," *J. Parasitol*, 84:983–991, 1998.

Marsh et al., "Molecular characterization and differentiation of *Sarcocystis falcatula* and *Sarcocystis neurona* isolates," *J. Parasitol*, 85:750–757, 1999.

Marsh et al., "Molecular and antigenic analysis of multiple *sarcocystis neurona* isolates obtained from horses with equine protozoal myeloencephalitis from different geographic regions," *J. Veterinary Internal Med.*, 14:12:330, 2000.

Marsh et al., "Characterization of a *Sarcocystis neurona* isolate from a Missouri horse with equine protozoal myeloencephalitis," *Vet Parasitol* 95: 143–154, 2001.

Nakamura et al., In: *Enzyme Immunoassays: Heterogeneous and Homogeneous Systems*, Chapter 27, 1987.

O'Shannessy et al., *J. Immun. Meth.*, 99, 153–161, 1987.

Owens and Haley, *J. Biol. Chem.*, 259:14843–14848, 1987.

Parmley et al., "Two alleles of the gene encoding surface antigen p22 in 25 strains of *Toxoplasma gondii*," *J. Parasitol*, 80:293–301, 1994.

Potter and Haley, *Meth. Enzymol.*, 91, 613–633, 1983.

Ramos-Vara et al., "Optimization of immunohistochemical methods using two different antigen retrieval methods on formalin-fixed paraffin-embedded tissues: experience with 63 markers," *J. Vet. Diagn. Invest.* 12:307–11, 2000.

Sabin, "Toxoplasmic encephalitis in children," *J. Am Med Assoc.*, 116:801–814, 1941.

Suedmeyer et al., "Acute pulmonary *Sarcocystis falcatula* infection in three victoria crown pigeons (*Gouru Victoria*) housed indoors," *J. Zoo Wildl. Med.* (in press), 2002.

Ware et al., "Strain-specific antigens of *Toxoplasma gondii*," *Infect. Immun.*, 55:778–783, 1987.

Woodward et al., "Detection of monoclonal antibodies specific for carbohydrate epitopes using periodate oxidation," *J. Immunol. Methods*, 78: 143–153, 1985.

What is claimed is:

1. A monoclonal antibody that binds immunologically to a *Sarcocystis neurona* organism or antigen, designated 2A7-18, deposited with the ATCC as PTA-3418, or 2G5-2, deposited with the ATCC as PTA-3419.

2. The monoclonal antibody of claim 1, wherein said antibody is designated 2A7-18, deposited with the ATCC as PTA-3418.

3. The monoclonal antibody of claim 1, wherein said antibody is designated 2G5-2, deposited with the ATCC as PTA-3419.

4. The monoclonal antibody of claim 1, wherein said antibody comprises a label.

5. The manoclonal antibody of claim 4, wherein said label is a radioisotope, bead, a ligand, a chemilluminescent molecule, a fluorescent molecule, or an enzyme.

6. The monoclonal antibody of claim 1, wherein said antibody comprises a therapeutic compound.

7. The monoclonal antibody of claim 6, wherein said therapeutic compound is a radioisotope or a chemotherapeutic.

8. A kit comprising at least one a monoclonal antibody that binds immunologically to a *Sarcocystis neurona* organism or antigen, designated 2A7-18, deposited with the ATCC as PTA-3418, or 2G5-2, deposited with the ATCC as PTA-3419, in a suitable container.

9. The kit of claim 8, comprising both 2A7-18, deposited with the ATCC as PTA-3418, and 2G5-2, deposited with the ATCC as PTA-3419, in suitable containers.

10. The kit of claim 8, wherein said antibody comprises a label.

11. The kit of claim 10, wherein said label is a bead, a radioisotope, a ligand, a chemilluminescent molecule, a fluorescent molecule, or an enzyme.

* * * * *